(12) United States Patent
Matsumoto

(10) Patent No.: US 8,760,656 B2
(45) Date of Patent: *Jun. 24, 2014

(54) FLUORESCENCE DETECTION APPARATUS

(75) Inventor: Kazuhiro Matsumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 88 days.

This patent is subject to a terminal disclaimer.

(21) Appl. No.: 12/572,540

(22) Filed: Oct. 2, 2009

(65) Prior Publication Data

US 2010/0019158 A1    Jan. 28, 2010

Related U.S. Application Data

(63) Continuation of application No. 12/031,308, filed on Feb. 14, 2008, now Pat. No. 7,619,733.

(30) Foreign Application Priority Data

Feb. 21, 2007   (JP) ................................. 2007-040902

(51) Int. Cl.
*G01N 21/25* (2006.01)

(52) U.S. Cl.
USPC ......................................................... 356/417

(58) Field of Classification Search
USPC ........................................ 356/317–318, 417
See application file for complete search history.

(56) References Cited

U.S. PATENT DOCUMENTS

| | | | |
|---|---|---|---|
| 4,516,856 A | 5/1985 | Popelka | |
| 5,834,758 A | 11/1998 | Trulson et al. | |
| 5,894,347 A | 4/1999 | MacDonald | |
| 6,043,880 A * | 3/2000 | Andrews et al. | 356/417 |
| 6,295,172 B1 | 9/2001 | Yamamichi et al. | |
| 6,692,125 B2 | 2/2004 | Matsumoto | |
| 7,619,733 B2 * | 11/2009 | Matsumoto | 356/318 |
| 2003/0160151 A1 | 8/2003 | Zarate et al. | |
| 2005/0018253 A1 | 1/2005 | Takeda | |
| 2006/0226375 A1 | 10/2006 | Maruo | |

FOREIGN PATENT DOCUMENTS

| | | |
|---|---|---|
| JP | 3116397 | 10/2000 |
| JP | 2003-078820 | 3/2003 |
| JP | 2005-045552 | 2/2005 |

* cited by examiner

*Primary Examiner* — Kara E Geisel

(74) *Attorney, Agent, or Firm* — Fitzpatrick, Cella, Harper & Scinto

(57) ABSTRACT

Fluorescence detection apparatus detects fluorescence from a fluorescent object. The apparatus includes a light source configured to irradiate the fluorescent object with light, a shutter configured to block the light, from the light source, directed to the fluorescent object, an optical output measuring unit arranged in an optical path between the shutter and the light source, an image pickup element configured to detect the fluorescence from the fluorescent object and to capture a noise image, and a changing unit configured to change at least one of an accumulation time of the image pickup element and an open-close time of the shutter. The changing unit calculates the accumulation time for capturing the noise image using the measurement result of the optical output measuring unit, and corrects a captured fluorescent image generated by detecting the fluorescence, using the noise image captured during the accumulation time calculated by the calculation unit.

9 Claims, 10 Drawing Sheets

FIG. 7A

IMAGE DATA OF FIXED PATTERN
NOISE FOR ACCUMULATION TIME td
Nd_td (i, j)

| td(1,1) | td(1,2) | td(1,3) | td(1,4) |
|---------|---------|---------|---------|
| td(2,1) | td(2,2) | td(2,3) | td(2,4) |
| td(3,1) | td(3,2) | td(3,3) | td(3,4) |
| td(4,1) | td(4,2) | td(4,3) | td(4,4) |

FIG. 7B

IMAGE DATA OF FIXED PATTERN
NOISE FOR ACCUMULATION TIME t1
Nd_t1 (i, j)

| t1(1,1) | t1(1,2) | t1(1,3) | t1(1,4) |
|---------|---------|---------|---------|
| t1(2,1) | t1(2,2) | t1(2,3) | t1(2,4) |
| t1(3,1) | t1(3,2) | t1(3,3) | t1(3,4) |
| t1(4,1) | t1(4,2) | t1(4,3) | t1(4,4) |

FIG. 7C

IMAGE DATA OF FIXED PATTERN
NOISE FOR ACCUMULATION TIME ti
Nd_ti (i, j)

| ti(1,1) | ti(1,2) | ti(1,3) | ti(1,4) |
|---------|---------|---------|---------|
| ti(2,1) | ti(2,2) | ti(2,3) | ti(2,4) |
| ti(3,1) | ti(3,2) | ti(3,3) | ti(3,4) |
| ti(4,1) | ti(4,2) | ti(4,3) | ti(4,4) |

FIG. 7D

IMAGE DATA OF READ NOISE
Nd_ro (i, j)

| ro(1,1) | ro(1,2) | ro(1,3) | ro(1,4) |
|---------|---------|---------|---------|
| ro(2,1) | ro(2,2) | ro(2,3) | ro(2,4) |
| ro(3,1) | ro(3,2) | ro(3,3) | ro(3,4) |
| ro(4,1) | ro(4,2) | ro(4,3) | ro(4,4) |

FIG. 10

TIME TABLE

0:30 TURN ON LASER
0:50 MEASURE LASER OUTPUT
1:00 CAPTURE DARK IMAGE

FLUORESCENCE DETECTION APPARATUS

This is a continuation of U.S. Pat. Ser. No. 12/031,308, filed Feb. 14, 2008, which issued as U.S. Pat. No. 7,619,733, on Nov. 17, 2009.

BACKGROUND OF THE INVENTION

1. Field of the Invention

The present invention relates to a fluorescence detection apparatus that detects fluorescence from a fluorescent object. In particular, the present invention is applied to a fluorescence detection apparatus used for clinical tests such as DNA analysis.

2. Description of the Related Art

In an apparatus for imaging a fluorescence intensity of a marker of a target DNA bound with a probe of a DNA chip, a method is known in which fluorescent images are collectively captured with a long exposure because the fluorescence emitted from a marker is weak. Unfortunately, when the long exposure is performed, dark current may be generated in a sensor, causing a noise in an image. To avoid this, a cold charge-coupled device (CCD) has been used.

To remove the noise without a cold CCD, a method is known in which a noise image is generated while preventing light from entering an object after the object is captured with a long exposure, and the noise image is subtracted from the captured image of the object for its correction. For example, this is a method in which a noise image accumulated for a time equivalent to the exposure time is captured while a shutter is closed, and the noise image is subtracted from the captured image.

Also, there are known configurations that remove fixed pattern noise during a long exposure by using a dark image captured before the object is captured. Such configurations include: [1] a camera that previously acquires a plurality of dark images for a time shorter than an accumulation time calculated on the basis of a photometric value of an object, and obtains a dark image captured during the accumulation time, to reduce an acquisition time of the dark image (see Japanese Patent Laid-Open No. 2005-45552), and [2] a camera that captures dark images for an accumulation time calculated on the basis of a photometric value of an object before and after the actual capturing, to perform image correction by using both images (see Japanese Patent Laid-Open No. 2003-78820).

Also, an image converting and recording apparatus is known which measures the brightness of the outside through a photometric window, and calculates the accumulation time of a CCD (see Japanese Patent No. 03116397).

However, with these conventional examples, the method using the cold CCD is not practical because the cold CCD is extremely expensive, and hence, the apparatus may be expensive.

In contrast, an effective method is one, in which the light from the object is blocked, the noise image caused by an image pickup element or a peripheral circuit is captured and a fixed pattern noise image is generated, to correct the object image. The fixed pattern noise image may vary depending on the accumulation time of the image pickup element. Thus, the method captures the noise image for the accumulation time equivalent to that for capturing the object. The noise image for the accumulation time equivalent to that for capturing the object can be captured after the image of the object is captured. This may provide an accurate fixed pattern noise image. However, capturing the noise image after capturing the object requires time for correcting the fixed pattern noise, thereby increasing the testing time. This configuration is not practical when a large number of samples have to be measured.

Another issue to be considered is that the noise image captured while the light from the object is blocked contains a fixed pattern noise and a random noise. Since the random noise may vary depending on an image, the influence of the random noise should be removed and only the fixed pattern noise should be used for correction, to obtain a further accurate fluorescent image. To obtain this image, an effective method is one, in which a fixed pattern noise image is generated by capturing and averaging a plurality of dark images. However, capturing the plurality of dark images may require time. Further, if images of a plurality of DNA chips are captured, capturing a plurality of dark images for each DNA chip may require more time.

Therefore, the fixed pattern noise image has to be generated before the fluorescence is captured. It is, however, difficult to calculate the accumulation time in such an arrangement.

Japanese Patent Laid-Open No. 2005-45552 discloses a method in which the brightness of an object to be captured is measured through a taking lens. Prior to that image capture, the method sets two types of accumulation times, which are calculated on the basis of the measured light quantity and shorter than the exposure time for image-capturing. Then, non-exposure images previously captured during the accumulation times are used to correct the fixed pattern noise. However, when a dark image for a predetermined time is calculated using the dark images captured during the different accumulation times, the influence of the random noise may be enhanced. To remove the random noise, a larger number of dark images have to be taken.

In addition, the color of the fluorescent marker may fade, and the fluorescence intensity may deteriorate because of the irradiation of the exciting light. Thus, to measure accurately, light should not be emitted before the measurement. The brightness of the object cannot be previously measured through the taking lens, and thus, the accumulation time cannot be calculated.

In addition, as long as the exposure time is determined by using the brightness of the object, an image having a constant integration value of the light quantity is captured. It is not possible to obtain an image which has an absolute value of the fluorescent brightness for each probe.

Japanese Patent Laid-Open No. 2003-78820 is similar to the above in that the exposure amount is determined on the basis of the brightness of an object.

Also, with the method disclosed in Japanese Patent No. 03116397, which detects the brightness of the circumference using a built-in sensor, the accurate light quantity for illuminating the object (in this case, a silver-halide film) is not detected. Thus, it is difficult to obtain an accurate fluorescent image.

If the exciting light source excites the fluorescent marker with a constant brightness, a noise image and a fluorescent image can be captured during a predetermined accumulation time. However, such a laser source (in particular, a solid laser source with a constant output) is expensive, and the cost of a product with such a laser source may be expensive. On the other hand, the output of a low-cost laser source may vary due to the influence of temperature, heat-radiation environment, and the like, and may deteriorate with lighting time, thereby hardly providing stable illumination.

SUMMARY OF THE INVENTION

As mentioned above, various improvements have been made to detect weak fluorescence in the conventional configurations; however, these improvements are insufficient. In light of this, the present invention provides a fluorescence detection apparatus that accurately detects weak fluorescence.

The present invention provides an emission detection apparatus that detects emission from an emission object. The apparatus includes a light source configured to irradiate the emission object with light, a shutter configured to block the light from the light source, an optical output measuring unit configured to detect the light from the light source, an image pickup element configured to detect the emission from the emission object, and a changing unit configured to change at least one of an open-close time of the shutter and an accumulation time of the image pickup element, on the basis of the measurement result of the optical output measuring unit.

Also, more specifically, the present invention provides a fluorescence detection apparatus that detects fluorescence from a fluorescent object. The apparatus includes a light source configured to irradiate the fluorescent object with light, a shutter configured to block the light, from the light source, directed to the fluorescent object, an optical output measuring unit arranged in an optical path between the shutter and the light source, an image pickup element configured to detect the fluorescence from the fluorescent object and to capture a noise image, and a changing unit configured to change at least one of an accumulation time of the image pickup element and an open-close time of the shutter. The changing unit has a calculation unit configured to calculate the accumulation time for capturing the noise image on the basis of the measurement result of the optical output measuring unit, and a correction unit configured to correct a captured fluorescent image that is generated by detecting the fluorescence, using the noise image captured during the accumulation time calculated by the calculation unit.

Further, the present invention provides an apparatus that acquires a dark image. The apparatus includes an optical output measuring unit configured to detect light from a light source, and a changing unit configured to change an accumulation time of an image pickup element on the basis of the measurement result of the optical output measuring unit. The image pickup element acquires the dark image on the basis of the accumulation time.

With the optical output measuring unit, light with a constant light quantity can be emitted on the fluorescent object, thereby easily removing a noise, and accurately detecting the fluorescence.

In another embodiment, the present invention is directed to a method of operating an emission detection apparatus. Preferably, the emission detection apparatus used in the method includes a light source configured to irradiate an emission object with light, a shutter positioned between the light source and the emission object, and an image pickup element configured to capture both the emission image from the emission object when irradiated with light from the light source and a dark image prior to irradiation. The method includes a step of activating the light source to emit light, with the shutter closed. There is also a step of measuring light from the light source in an optical path position between the shutter and the light source. A calculation step calculates an accumulation time of the image pickup element for at least one of capture of the dark image and capture of the emission image. The calculated accumulation time is based on the measurement in the measurement step. The method may further include capturing the dark image for the dark image accumulation time and, after capturing the dark image, opening the shutter to irradiate the emission object. A second detecting step may include detecting emission from the emission object using the image pickup element, wherein at least one of the open-close time of the shutter and the pickup time of the image pickup element is determined based on the accumulation time for the emission image calculated in the calculation step.

Further features of the present invention will become apparent from the following description of exemplary embodiments with reference to the attached drawings.

BRIEF DESCRIPTION OF THE DRAWINGS

FIGS. 7A to 7D are tables showing pixel values of images.
FIG. 10 is an illustration of a time table.

DESCRIPTION OF THE EMBODIMENTS

Figure 1:
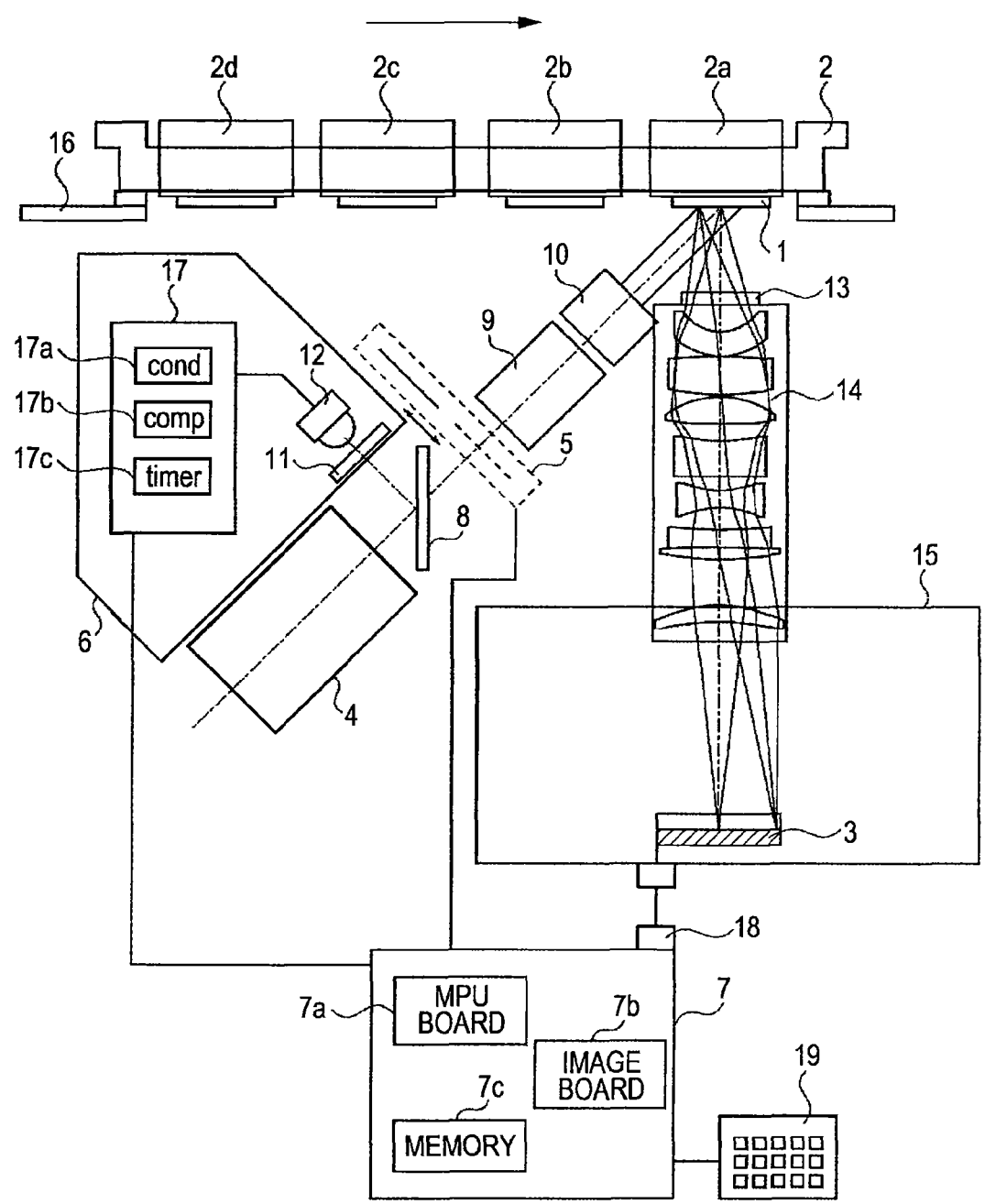
FIG. 1 is a block diagram showing a fluorescence detection apparatus according to an embodiment.

Embodiment
The present invention will be described in detail with illustrated embodiments.
(Apparatus Configuration)
FIG. 1 is a block diagram showing a fluorescence detection apparatus according to an embodiment of the present invention.

A fluorescent object 1 is previously placed on a cassette tray 2. An image pickup element 3 detects fluorescence of the fluorescent object 1. A laser source 4 irradiates the fluorescent object 1 with light. A shutter 5 blocks light directed to the fluorescent object 1. An optical output measuring unit 6 is disposed between the shutter 5 and the laser source 4. A control circuit (changing unit) 7 changes at least one of an accumulation time of the image pickup element 3 and an open-close time of the shutter 5. The control circuit 7 has a micro processing unit (MPU) board (calculation unit) 7a that calculates the accumulation time for capturing a noise image, on the basis of the measurement result of the optical output measuring unit 6. The control circuit 7 also has an image board (correction unit) 7b that corrects a captured image generated by detecting the fluorescence thereof, using the noise image captured during the accumulation time calculated on the basis of the calculation result of the MPU board 7a.

The fluorescent object 1 is used in this embodiment, however, a phosphorescent object that emits phosphorescence can be also used, namely, an emission object and an emission detection apparatus may be used. The optical output measuring unit 6 in this embodiment is a feature of the invention. A change signal to change a setting time (the accumulation time of the image pickup element 3 or the open-close time of the shutter 5) is transmitted on the basis of the measurement result of the optical output measuring unit 6, and together with the control circuit (changing unit) 7 that changes the setting time, proper setting is achieved. Since the accumulation time of the image pickup element 3 has been determined, the image pickup element 3 can previously detect a dark image to be obtained in advance of detection of the irradiated object, and a memory 7c can store the detected dark image.

Specific and detailed configuration of an embodiment of the invention is described below.

The laser source 4, which is a solid laser source, generates a laser beam having a wavelength of 532 nm. A beam splitting mirror 8 has a single layer film of $MgF_2$ on its incident side, and an antireflection film on its back side. The single layer film on the front side reflects the laser beam with the wavelength of 532 nm by approximately 2%, whereas the antireflection film on the back side transmits the light by approximately 100%. The shutter 5 controls irradiation and non-irradiation of the laser beam. A beam expander 9 expands the beam diameter of the laser beam. A beam homogenizer 10 converts the laser beam, which is a Gaussian beam, into a flattop light beam with a uniform intensity at an object plane. The shutter 5, the beam expander 9, and the beam homogenizer 10 constitute an illumination optical system. In addition, a diffusion plate 11 made of, for example, opal glass or frosted glass, and a photodetector 12 are disposed in a splitting direction of the beam splitting mirror 8. The diffusion plate 11 and the photodetector 12 constitute a laser output measuring unit. A fluorescent filter 13, an image pickup optical system 14, and a digital camera 15 having the image pickup element 3 constitute a fluorescence image pickup unit. A cassette tray 2 is disposed on a carrying stage 16, and is located above the image pickup optical system. The cassette tray 2 has a plurality of cassettes 2a, 2b, 2c and 2d, each having a DNA probe array with fluorescent markers. Fluorescence emitted from the DNA probe array with the fluorescent markers passes through the image pickup optical system 14, and is guided to the image pickup element 3.

An optical output measurement circuit 17 receives the output from the photodetector 12. The optical output measurement circuit 17 has a condenser 17a that accumulates electric charges, a comparator 17b that compares the voltage of the condenser 17a with a predetermined value, and a timer 17c that measures a time necessary for the voltage to reach the predetermined value. The control circuit 7 has the MPU board 7a, the image board 7b, and the memory 7c. The memory 7c stores the measured time. These procedures are performed with a personal computer. The control circuit 7 determines the change of the accumulation time of the image pickup element 3 or the open-close time of the shutter 5, and transmits its signal to the image pickup element 3 or the shutter 5. The control circuit 7 changes the image-capturing time of the digital camera 15, and transfers an image from the digital camera 15, through a control interface 18. The control circuit 7 is connected to an operation panel 19. Operations, such as ON/OFF of a power supply, starting of measurement, inputting of the number of analytes, and the like, are input to the control circuit 7 through the operation panel 19.

Embodiments

First Embodiment (Fluorescence Detection Apparatus with Laser Irradiation Time Not Equivalent to Accumulation Time of Fluorescent Image)

Next, a method of capturing a marker fluorescent image on the DNA chip is described using the apparatus having the above configuration. Before preparation for hybridization reaction, etc., of the DNA chip, an operator operates the operation panel 19 to supply power to the apparatus. After the power is ON, the control circuit 7 initializes the apparatus, and turns ON the power of the laser source 4. The laser source 4 emits a laser beam.

(Accumulation Time Calculation)

After the waiting time, in which the laser output becomes a given stable state, has elapsed, the optical output measuring unit 6 measures the output of the laser beam.

FIG. 2(A) shows output variation of the solid laser source 4. In the drawing, the horizontal axis plots time, and the vertical axis plots laser output. For example, in FIG. 2(A), the laser output is shown in a range from 80 to 100 mW. As shown in the drawing, the solid laser source 4 has a plurality of stable states depending on the temperature, humidity, environmental conditions, and the like. A discrete output variation as shown in a part 2-A-1, an unstable output variation as shown in a part 2-A-2, etc. may appear. When the power is turned ON again, the output may have a different stable state. As the apparatus is used for a long period, the output may gradually decreases. Also, immediately after the laser is tuned ON, a time (waiting time) is necessary for stabilization. In FIG. 2(A), the waiting time has elapsed. FIG. 2(C) is a timing chart showing opening and closing of the shutter 5. The shutter 5 is closed during the laser output measurement. In this state, the laser beam would not excite a fluorescent marker. The control circuit 7 has, in the memory 7c, a predetermined accumulation voltage Vc concerning the ISO speed ratings and the like of the digital camera 15. Before the laser output measurement is started, the control circuit 7 sets the predetermined voltage Vc to the comparator 17b. Then, the timer 17c is started when the laser output measurement is started. The light having the wavelength of 532 nm emitted from the laser source 4 is partially reflected by the surface of the beam splitting mirror 8, and illuminates the diffusion plate 11. The light scatters at the diffusion plate 11, and partially reaches the photodetector 12 to be converted into current. Since the measurement is performed through the diffusion plate 11, the laser output can be stably measured while the influence such as an angular variation of the beam can be reduced. The condenser 17a accumulates the current. The comparator 17b can use the voltage for comparison at any timing. FIG. 2(B) is a timing chart showing the voltage of the condenser 17a. When the measurement is started, the voltage increases and reaches the predetermined voltage Vc. The timer 17c measures a time tp from when the accumulation is started to when the voltage reaches the predetermined voltage Vc. The signal of the time tp is transferred to the control circuit 7, and stored in the memory 7c. The control circuit 7 calculates an accumulation time td for capturing a dark image for the correction, and calculates an accumulation time tf for capturing a fluorescent image, on the basis of the time tp. The actual exposure time may extend by an intensity variation of the laser beam. Hence, the actual exposure time may be longer than the calculated time by about 15%, or by the amount of the intensity variation of the laser beam.

That is, the exposure time is expressed as follows:

$$td=tf=tp+\delta t$$

If the laser output is stable, the output current of the photodetector 12 may be converted into a voltage, and the voltage may be used for measuring the laser output. When a laser source with an output variation is used like the embodiment, the accumulation should be performed for a given time, and the measurement should be performed after the influence of the variation with a high frequency is removed, to perform further accurate measurement. This configuration allows light to be accumulated during the irradiation of the light on the fluorescent object.

(Dark Image Capturing)

Next, a dark image, which is a noise image used for correction of a fluorescent image, is captured. The dark image is captured in a dark state with no light input on an image pickup element, and is electrical noise.

The control circuit 7 performs communication through the control interface 18, starts the accumulation in the image pickup element 3 of the digital camera 15, transmits an instruction to determine the accumulation when the time td has elapsed, transfers the image to the image board 7b of the control circuit 7, and stores the image in the memory 7c. FIG. 2D is a timing chart showing the state of the accumulation of the image pickup element 3. A part H indicates the accumulation. In this embodiment, the operation is repeated three times to obtain three dark images di1, di2, and di3 for the accumulation time td. The control circuit 7 averages these images, removes random noise, generates a fixed pattern noise image Id, which is a noise image, and stores the generated fixed pattern noise image Id in the memory 7c. This completes the preparation for capturing the fluorescence. Also, while the number of dark images may be one, a plurality of dark images are desirable to increase the accuracy of the dark image.

If the operation for capturing the fluorescence is not performed for a given time, the control circuit 7 measures the laser output again, captures dark images, and updates the fixed pattern noise image Id in the memory 7c. When the operator operates the operation panel 19 to perform an operation for detecting the fluorescence such as opening a cover of a dark box (not shown), the operation for capturing the dark image is terminated. The dark image may be continuously captured during installation of the cassette tray 2 or during setting of the DNA chip, until just before the fluorescence is actually captured.

A program may be provided such that the dark image is captured if the variation in the laser output is a predetermined value or greater, so as to reduce the number of times of capturing the dark images. The number of times of capturing the dark images should be determined depending on the variation in the laser output to be used.

In this embodiment, while a plurality of dark images are captured and these images are used to obtain one fixed pattern noise image, if there is only one dark image, this dark image may be directly used as a fixed pattern noise image for the correction.

(Fluorescence Capturing)

The operator sets a DNA chip, which has been prepared for hybridization reaction and the like, on the cassette tray 2, operates the operation panel 19, opens the cover of the dark box (not shown), installs the cassette tray 2, and starts capturing the fluorescence. The control circuit 7 detects the capturing of the fluorescence through the input to the operation panel 19. If the control circuit 7 detects capturing of the fluorescence during capturing of a dark image, it interrupts the capturing operation, closes the cover of the dark box, and prepares for capturing the fluorescence such that the cassette 2a is positioned above the image-capturing optical axis. The control circuit 7 starts the accumulation with the image pickup element 3, and then, opens the shutter 5. FIG. 2(C) shows a timing chart of opening and closing of the shutter 5. The beam expander 9 expands the laser beam. The beam homogenizer 10 converts the light beam into a light beam having a uniform intensity distribution in the cross section of the beam at an object plane, so as to excite the fluorescent marker of the DNA chip. The fluorescent filter 13 blocks the reflected light and the scattering light of the exciting light, and transmits only the fluorescence emitted from the marker. The image pickup optical system 14 forms an image of the fluorescence on the image pickup element 3, thereby generating a fluorescent image.

Figure 2:
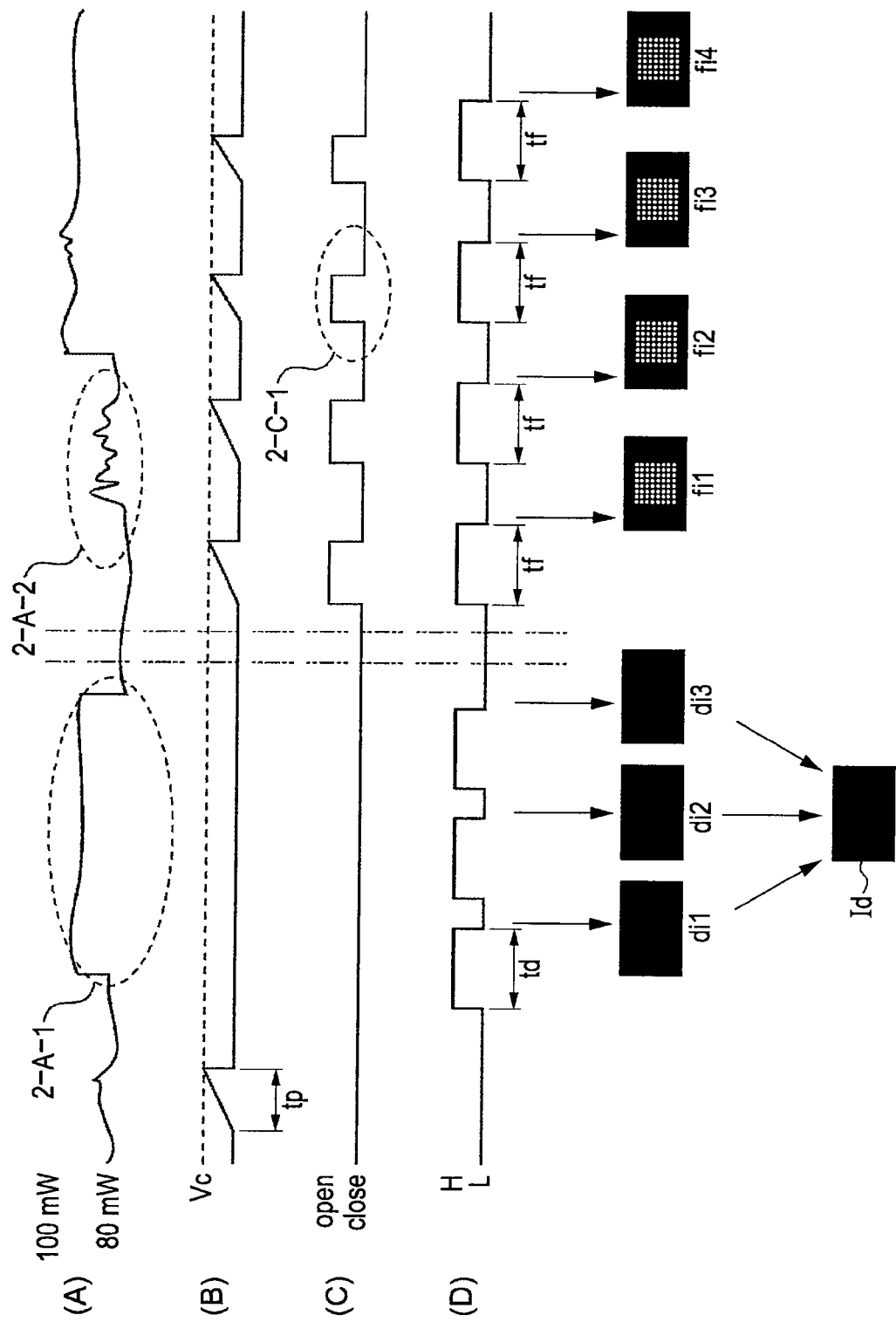
FIG. 2 is a timing chart of a first embodiment.

The photodetector 12 receives the laser beam split by the beam splitting mirror 8, and converts the received energy into current. The condenser 17a accumulates the current. The condenser 17a transmits a signal to the control circuit 7 when the accumulated current reaches the predetermined voltage Vc, and discharges the electric charge accumulated in the condenser 17a. When the control circuit 7 receives the signal, the control circuit 7 closes the shutter 5. The excitation of the fluorescent marker is terminated. The image pickup element 3 continues accumulation until the accumulation time tf obtained through the calculation elapses. When the accumulation time tf has elapsed, the accumulation is terminated. The fluorescent image If is transferred to the control circuit 7. The control circuit 7 controls the carrying stage 16 to position the second cassette 2b on the image-capturing optical axis. The image pickup element 3 starts accumulation, the shutter 5 is opened, and the fluorescent marker is excited, similarly to the above description. As shown in FIG. 2, the condenser 17a accumulates the laser beam, the shutter 5 is closed at the time when the voltage reaches the predetermined voltage Vc, and the excitation is terminated, similarly to the above description. The accumulation is terminated and the image is transferred to the control circuit 7 when the accumulation time of the image pickup element 3 has reached the predetermined accumulation time tf. The control circuit 7 positions the third DNA chip on the image-capturing optical axis to capture the fluorescence, as discussed above. As shown in FIG. 2(C), the laser output at this time increases, and hence the voltage of the condenser 17a reaches the predetermined voltage Vc in a shorter time. Therefore, the opening time of the shutter 5 is short as shown in a part 2-C-1 in FIG. 2(C). The accumulation time of the image pickup element 3 continues for the accumulation time tf obtained through the calculation. The fluorescent image is transferred to the control circuit 7 when the accumulation is terminated. As described above, the exposure time of the laser beam may vary depending on the laser intensity; however, the accumulation time of the image pickup element 3 is always constant. Because of this, the fixed pattern noise image initially generated can be used for correction. Accordingly, an analytic image can be generated promptly.

(Image Correction)

Figure 3:
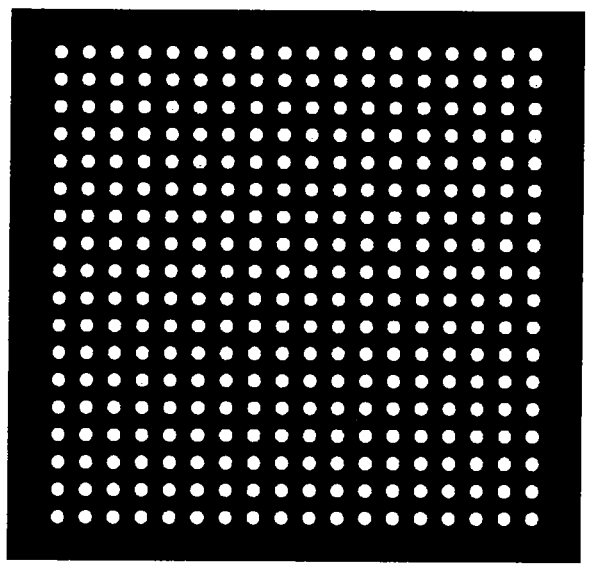
FIG. 3 is an illustration of a fluorescent image.

The control circuit 7 subtracts the fixed pattern noise image Id obtained above, from the fluorescent image If, to generate an analytic fluorescent image. FIG. 3 is an illustration showing a fluorescent image in which images of fluorescent probes of a DNA chip is captured. The parts of the DNA chip corresponding to the fluorescent probes are arrayed as bright parts, and the background appears black. The black part contains a fixed pattern noise component caused by the image pickup element 3. Thus, correction is required.

Figure 4A:
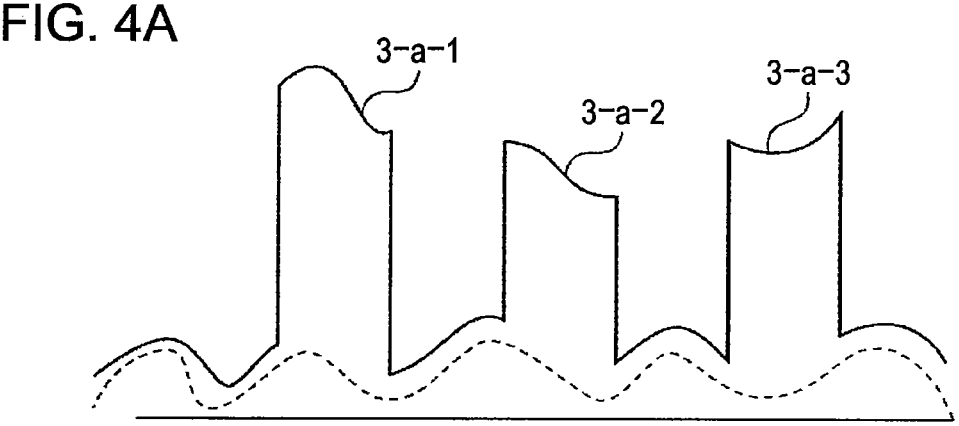
FIGS. 4A to 4C are diagrams showing a fluorescent image and a fixed pattern noise image.

FIG. 4A is a cross section of an image in which the fluorescence is captured. Such an image is obtained such that the vertical axis plots the brightness of the image.

Figure 4B:
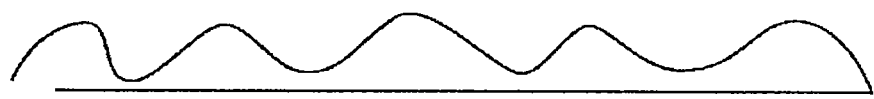
Figure 4C:
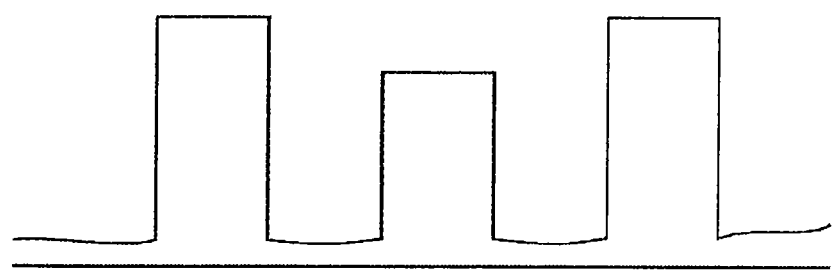

Parts 3-a-1, 3-a-2, and 3-a-3 of the DNA chip corresponding to fluorescent spots are shown as bright parts in FIG. 3, with high luminance. Thus, signals appear strongly. FIG. 4B is a cross section of the fixed pattern noise image Id at the same part. The fixed pattern noise can be removed by subtracting the fixed pattern noise image Id from the fluorescent image If. FIG. 4C is a cross section of the same part of the image in which the fixed pattern noise image Id has been subtracted from the fluorescent image If. Since the noise component has been removed, the contour of the fluorescent probe clearly appears.

Figure 5:
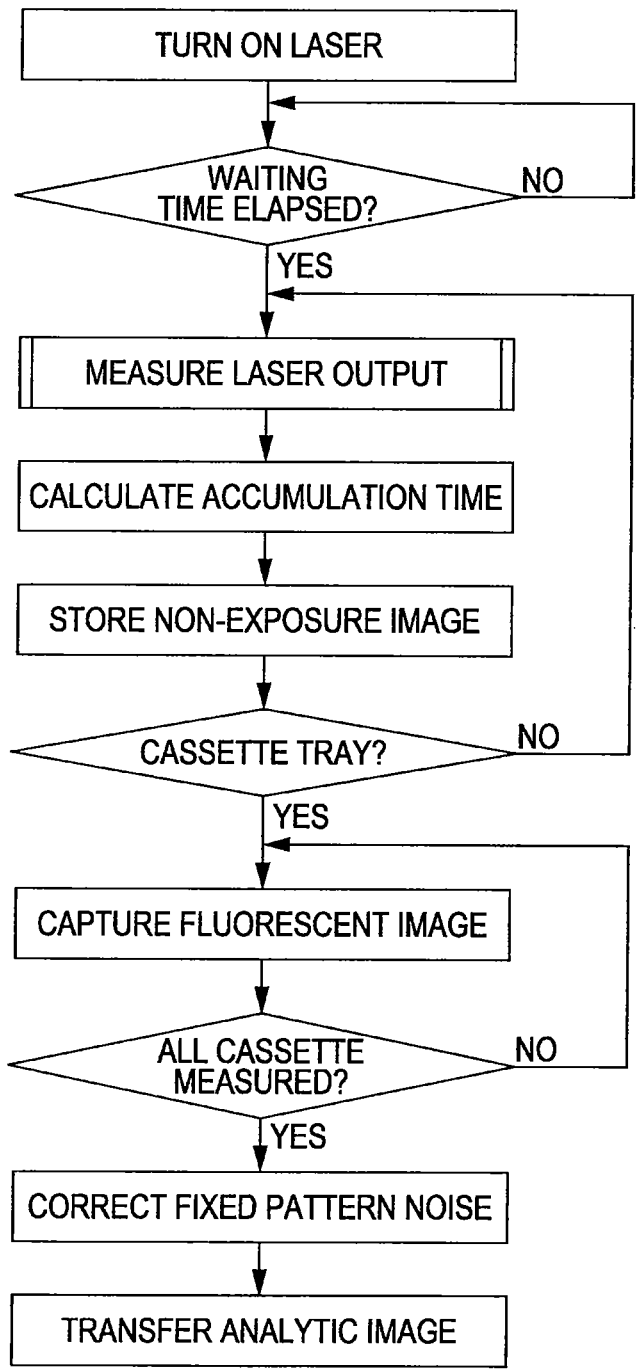
FIG. 5 is a flowchart showing an operation procedure.

The control circuit 7 is programmed to wait for a predetermined time after the power is supplied, and then to automatically perform the laser output measurement and the dark image capturing until the cassette 2a is installed. FIG. 5 is a flowchart showing the operation procedure.

As described above, the laser output is measured, the accumulation time is calculated on the basis of the measurement result, and the dark image is captured before the fluorescent is captured. Accordingly, the analytic image with the fixed pattern noise corrected can be generated immediately after the fluorescence is captured. Thus, the capturing can be efficient. In particular, when a plurality of objects are captured, the plurality of fluorescent images can be corrected by using a single fixed pattern noise image. Also, the fluorescence can be detected promptly.

In the exemplary embodiment, an integration value of the laser output is obtained during the accumulation by the image pickup element 3, and the open time of the shutter 5 is controlled. With this control, the capturing can be performed while the energy of the exciting light is kept constant. Accordingly, a measurement value with a highly reliable absolute value can be obtained. If the absolute value does not have to be so accurate, the shutter 5 may not be controlled, and the exciting laser beam may be emitted during the accumulation time. Still, since a non-exposure image is previously captured in the embodiment, the fixed pattern noise can be corrected immediately after the fluorescence is captured. Even in this case, the fixed pattern noise can be corrected immediately after the fluorescence is captured, and the analytic image can be efficiently obtained.

Second Embodiment (Fluorescence Detection Apparatus with Laser Irradiation Time Equivalent to Accumulation Time of Fluorescent Image)

In the first embodiment, the accumulation time during capturing the fluorescence is kept constant, and a single fixed pattern noise image is directly used for a fluorescent image of any cassette. Alternatively, the accumulation time may be controlled in accordance with the exposure time of the exciting light, the accumulation time may be recorded, and the fixed pattern noise image may be corrected, to be used for correcting the fluorescent image. This case is described below as a second embodiment.

Figure 6:
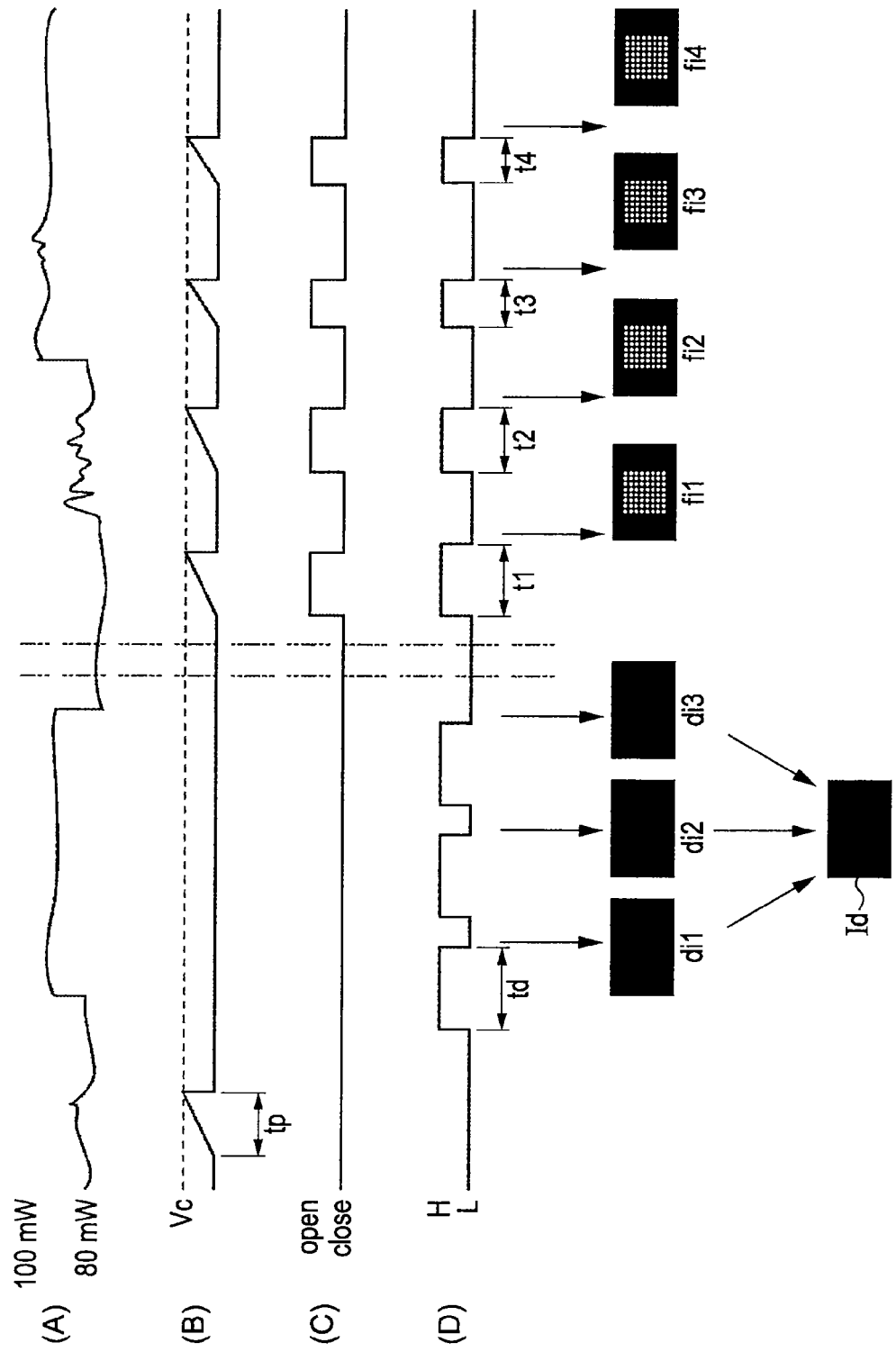
FIG. 6 is a timing chart of a second embodiment.

The configuration is similar to that of the first embodiment shown in FIG. 1. FIG. 6 shows a timing chart of the second embodiment. In this embodiment, a dark image is obtained in a manner similar to the first embodiment, however, the accumulation time during acquisition of the fluorescent image may vary depending on the laser output.

In particular, the measurement with the timer 17c is started and the shutter 5 is opened when the accumulation of the fluorescent image is started. Synchronously to this, the condenser 17a of the optical output measurement circuit 17 starts accumulating the current from the photodetector 12. The fluorescent marker is excited and the fluorescent image is accumulated in the image pickup element 3 while the shutter 5 is opened. When the voltage of the condenser 17a reaches the predetermined voltage Vc, the shutter 5 is closed, and the excitation of the marker is terminated. Synchronously to this, the control circuit 7 transmits an instruction for terminating the capturing to the digital camera 15 through the control interface 18, to terminate the accumulation of the image pickup element 3. The timer 17c has measured the time until the voltage of the condenser 17a reaches the predetermined voltage Vc, that is, the time from when the accumulation of the image pickup element 3 is started to when the accumulation is terminated. The timer 17c transmits the measured time to the control circuit 7 together with the image, and the memory 7c stores the time and the image. The capturing operation is performed for each cassette in a manner similar to the above, and the memory 7c stores images corresponding to the cassettes 2a to 2d, and accumulation times t1 to t4.

The control circuit 7 corrects the fixed pattern noise image in accordance with the accumulation times t1 to t4 of the captured images of the cassettes 2a to 2d.

In this embodiment, the optical output measuring unit 6 for obtaining the accumulation time for capturing the dark image also serves as a measuring unit for the integration value of the laser output during the excitation of the fluorescent marker. Accordingly, highly reliable measurement can be provided with a simple structure.

(Correction of Fixed Pattern Noise)

The fixed pattern noise image Id is obtained through the calculation by using the dark images di1, di2, and di3 captured during the accumulation time td. To accurately correct the fluorescent image, the fixed pattern noise image Id has to be corrected in accordance with the accumulation times t1 to t4 of the fluorescent images. FIG. 7A shows image data corresponding to each pixel of the fixed pattern noise image for the accumulation time td. Image data corresponding to an address (i, j) of each pixel is expressed as Nd_td(i, j). Also, a pixel value corresponding to each address of the fixed pattern noise image for the accumulation time t1 is expressed as Nd_t1(i, j) as shown in FIG. 7B. Hence, using the Nd_td(i, j) and the accumulation times t1 and td, Nd_t1(i, j) can be expressed as follows:

$$Nd\_t1(i,j)=Nd\_td(i,j)*t1/td$$

The fixed pattern noise has a dark current component and a read noise component. The dark current component is caused by the image pickup element 3, and has a size proportional to time. The read noise component depends on a reading circuit, and has a size which is not proportional to time. Hence, to be more accurate, an average read noise image Nd_ro(i, j) may be stored and calculation may be performed as follows:

$$Nd\_t1(i,j)=(Nd\_td(i,j)-Nd\_ro(i,j))*t1/td+Nd\_ro(i,j)$$

However, if the accumulation time is sufficiently long such as for capturing the fluorescence, the pixel value of the fixed pattern noise image may be approximated as being proportional to time. Performing calculation in a manner similar to the above, fixed pattern noise image data Nd_t1(i, j) to Nd_t4(i, j) respectively corresponding to the accumulation times t1 to t4 are obtained, and the obtained values are respectively subtracted from fluorescent image data fi1(i, j) to fi4(i, j), so as to correct each fixed pattern noise.

With this embodiment, the accumulation time in a non-exposure state can be omitted by synchronizing the open time of the shutter 5 with the accumulation time, thereby reducing the time necessary for the detection. In addition, since the fixed pattern noise image is corrected and used in accordance with the accumulation time of the image, efficient and highly reliable detection can be performed.

Third Embodiment (Apparatus Containing DNA Amplifier)

The above described embodiment is merely for the fluorescence detection apparatus. The advantages can be enhanced if the detection system is added to a gene diagnosis system that automatically performs a sequence of operations of analyte DNA amplification, fluorescence labeling, hybridization reaction, and detection. Consequently, systems to be added may include a DNA amplifying system, a labeling system, and a hybridization system. All or a part of these systems may be added.

Figure 8:
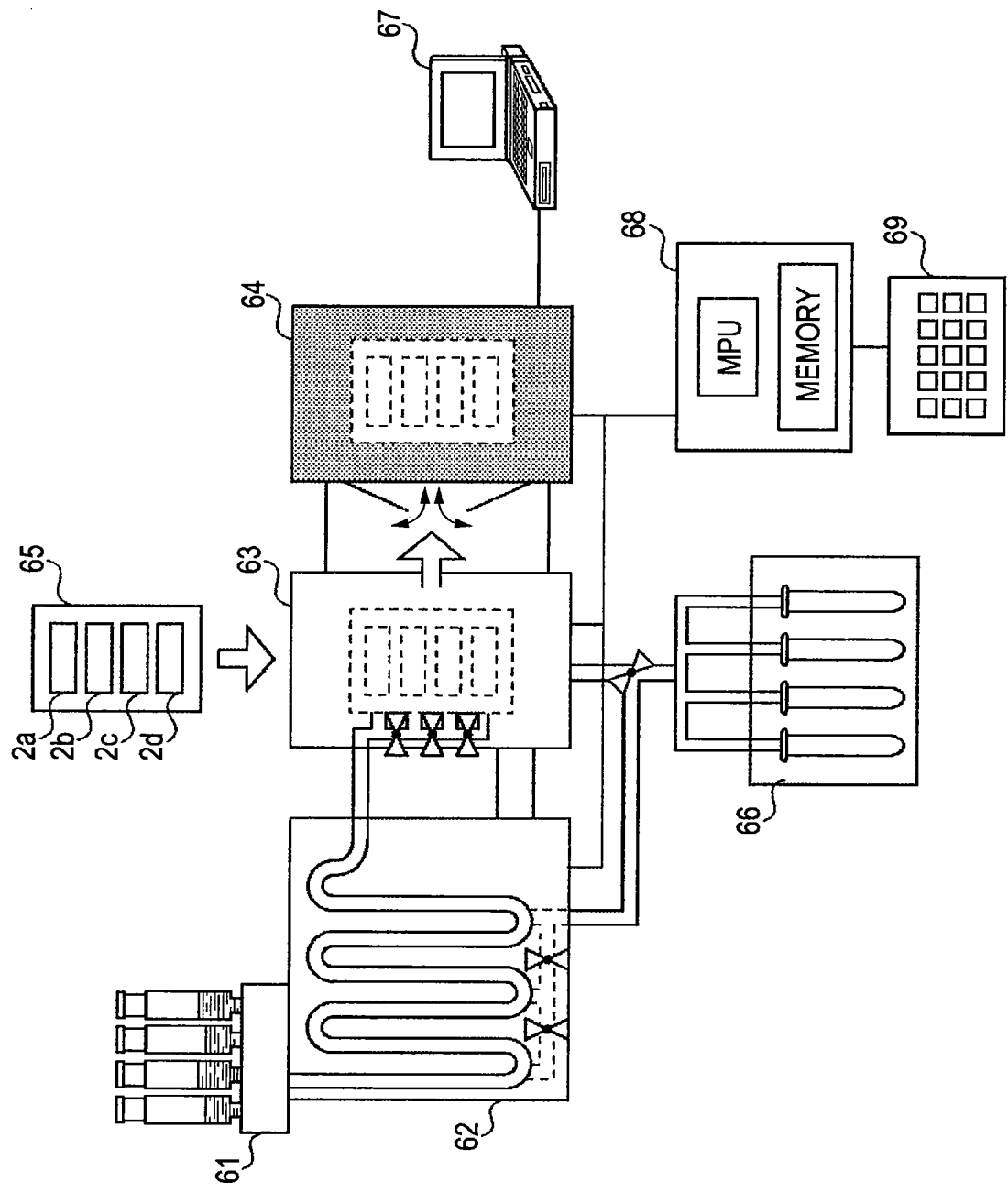
FIG. 8 is a block diagram showing a unit arrangement of a third embodiment.

FIG. 8 is a block diagram schematically showing an automatic system that collectively performs amplification of the analyte DNAs collected and extracted from living matter, detection of the fluorescence, and analysis. An analyte set unit 61 sets a pipette, a syringe, or the like, for inputting the analyte DNAs, and inserts the analyte DNAs. An amplification unit 62 amplifies the analyte DNAs. Accordingly, the number of the analyte DNAs markedly increases, and the analyte DNAs have binding reaction with marker fluorescent molecules. Then, the analyte DNAs are sent to a reaction unit 63 (hybridization system), and are hybridized with the probes of the DNA chip. A tray 65 provided with DNA chips 2a to 2d is installed to the reaction unit 63. A waste fluid control unit 66 processes waste fluid in the amplification unit 62. A reagent is applied to the reaction unit 63. A fluorescence detection unit 64 has the fluorescence detection apparatus of FIG. 1 in a dark box, so as to detect weak fluorescence. The fluorescence detection unit 64 captures an image of the marker fluorescent molecules bound with the DNA probes. The fluorescence detection unit 64 transmits an analytic image to a personal computer 67. The personal computer 67 uses the fluorescent image to perform DNA analysis. An operation panel 69 has various operation buttons.

Figure 9:
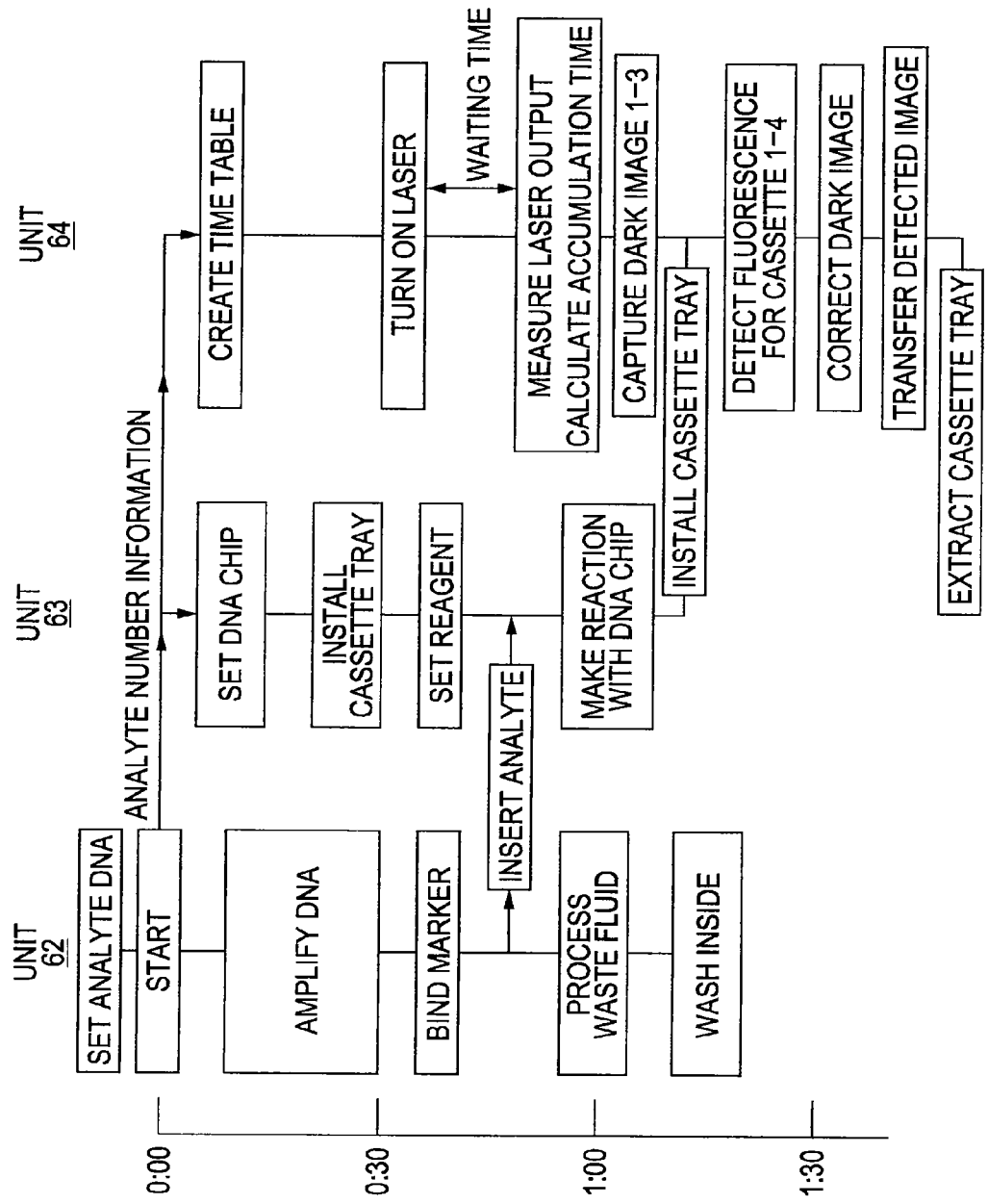
FIG. 9 is a timing chart of the third embodiment.

FIG. 9 shows an operation timing of each unit in the above configuration. An operator sets analyte DNAs on the analyte set unit 61, and operates the operation panel 69 to input the number of the analyte DNAs and to start the operation of the apparatus. Then, a control circuit 68 stores the number of the analyte DNAs in a memory with the start time. The control circuit 68 sets DNA chips on the tray 65 on the basis of the number of the analyte DNAs, and installs the tray 65 into the reaction unit 63. The amplification unit 62 starts amplifying the DNAs in a typical manner. In addition, the control circuit 68 creates a time table as shown in FIG. 10. The time table contains the laser-ON time, laser output measurement time, and dark image capturing start time, for the fluorescence detection unit 64. With this time table, the fluorescence detection start time is calculated on the basis of the amplification start time and the number of the analyte DNAs. A time necessary for each procedure is expected on the basis of the detection start time, to calculate the laser-ON time, the laser output measurement time, and the dark image capturing start time. The time required in the reaction unit 63 may slightly vary because of variations in time for setting a reagent, and time for temperature adjustment. The progress of each unit may be monitored, and the time table may be properly corrected for higher efficiency.

The analyte DNA amplified and bound with the fluorescent marker in the amplification unit 62 passes through a flow path, comes into contact with a DNA chip with a corresponding analyte identification number in the reaction unit 63, and is installed to a chamber in which a reagent has been set. The labeled analyte DNA is hybridized with a probe on the DNA chip, and is bound with a highly complementary probe. Thus, the highly complementary probe may be bound with the fluorescent marker, emitting strong fluorescence.

At the same time, the fluorescence detection unit 64 turns ON the laser, measures the laser output, and captures a dark image, on the basis of the preset time table.

After the dark image is captured, the tray 65 having the DNA chip after the hybridization reaction is installed to the dark box of the fluorescence detection unit 64, and the fluorescence is captured immediately. The fixed pattern noise of the detected image is corrected using the previously captured dark image according to the correction method described in the first or second embodiment. The corrected image is transferred to the personal computer 67 for analysis.

As described above, since the dark image has been obtained before the capturing of the fluorescent image being reacted in the reaction unit 63, after capturing the fluorescence, the noise image is corrected with the accumulation time for capturing the fluorescence. Accordingly, an analytic image with the fixed pattern noise corrected can be promptly generated. Thus, the time from when the amplification reaction is started to when the analysis result is displayed can be efficiently used, and accurate gene analysis can be performed.

Fourth Embodiment (Optional Configuration)

In the present invention, by using the optical output measuring unit 6, a weak signal can be accurately detected. In addition, to amplify the weak signal, a lock-in detection using a lock-in amplifier or the like may be additionally employed. For the lock-in detection, an optical modulation signal has to be generated. There are provided a method of generating a modulation signal with the laser source 4, a method of modulating with the shutter 5, and a method of providing an additional shutter for modulation between the laser source 4 and the fluorescent object 1. A drive signal for the modulation (modulation signal) is transmitted to the MPU board 7a. The fluorescent object excited with the modulated light emits fluorescence with a modulated intensity. The image pickup element 3 detects the fluorescence. The MPU board 7a obtains a signal for each pixel on the basis of a reference signal composed of the signal detected by the image pickup element 3 and the drive signal, to generate an image. If required, a MPU board as a calculation unit and a MPU board for calculation of the lock-in detection may be independently provided. With this configuration, a white noise can be reduced.

If a detection area is small, unbalanced detection may be employed in which light is separated into P-polarized light and S-polarized light, and an intensity difference therebetween is measured. In this case, a detector has to be provided for each pixel. For example, such detectors may be arranged in a line to scan a laser source.

Further, a laser source may be polarized into P-polarized light and S-polarized light, and emitted on a fluorescent object. In this case, light having a high emission intensity when being excited should be selected corresponding to the characteristics of a fluorescent material.

The DNA analysis using the apparatus of the invention may be applied to gene diagnosis in clinical test.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-040902, filed Feb. 21, 2007, which is hereby incorporated by reference herein in its entirety.

What is claimed is:

1. An apparatus for detecting emission from an object providing a reaction using DNA, comprising:
   a stage on which the object is disposed;
   a light source for irradiating a light to the object on the stage;
   an optical output measuring unit for detecting the light from the light source;
   an image pickup element for detecting the emission from the object; and
   a changing unit for changing at least one of an irradiation time to the object and an accumulation time of the image pickup element, on the basis of the measurement result of the optical output measuring unit.

2. An apparatus tor detecting a fluorescence image from an object providing a reaction using DNA, comprising:
   a stage on which the object is disposed;
   a light source for irradiating a light to the object on the stage;

an optical output measuring unit for detecting the light from the light source;

an image pickup element for detecting the fluorescence image from the object and capturing a noise image; and a changing unit for changing at least one of an irradiation time to the object and an accumulation time of the image pickup element, wherein the changing unit includes, a calculation unit configured to calculate the accumulation time for capturing the noise image on the basis of the measurement result of the optical output measuring unit, and a correction unit configured to correct a captured image that is generated by detecting the fluorescence image, using the noise image captured during the accumulation time calculated by the calculation unit.

3. The fluorescence detection apparatus according to claim 2,
wherein the light source emits exciting light that excites the object, and
wherein the fluorescence detection apparatus further comprises an image pickup unit having a fluorescence filter configured to transmit the fluorescence image from the object, to guide the fluorescence image to the image pickup unit, and to block the exciting light.

4. The fluorescence detection apparatus according to claim 2, wherein the light source is a laser source.

5. The fluorescence detection apparatus according to claim 2, wherein the changing unit allows a memory to store a waiting time, measures a time from when the light source is turned ON, and after the waiting time has elapsed, transmits a signal to start measuring the optical output from the light source.

6. The fluorescence detection apparatus according to claim 5, wherein the noise image is captured before the fluorescence image is detected and after the waiting time of the light source has elapsed.

7. The fluorescence detection apparatus according to claim 2, wherein a plurality of the objects are provided, and a plurality of captured images obtained from the plurality of objects are corrected on the basis of the noise image.

8. The fluorescence detection apparatus according to claim 2, wherein a plurality of images are captured prior to detection of fluorescence from the object, and a single noise image is generated using the plurality of images.

9. The emission detection apparatus according to claim 1, further comprising at least one of:
a DNA amplifying system configured to amplify an inserted DNA of living matter,
a labeling system configured to bind the amplified DNA with a marker fluorescent molecule; and
a hybridization system configured to bind the labeled DNA with a probe of a DNA chip.

* * * * *